United States Patent [19]

Griffith et al.

[11] Patent Number: 4,537,908
[45] Date of Patent: Aug. 27, 1985

[54] HERPES II TREATMENT

[75] Inventors: Ronald C. Griffith, Pittsford; Clyde R. Kinsolving, Fairport, both of N.Y.

[73] Assignee: Pennwalt Corporation, Philadelphia, Pa.

[21] Appl. No.: 425,138

[22] Filed: Sep. 27, 1982

Related U.S. Application Data

[63] Continuation-in-part of Ser. No. 277,777, Jun. 26, 1981, Pat. No. 4,351,847.

[51] Int. Cl.$^3$ .............................................. A61K 31/13
[52] U.S. Cl. ..................................... 514/659; 514/934
[58] Field of Search ............................................ 424/325

[56] References Cited

U.S. PATENT DOCUMENTS

| | | | |
|---|---|---|---|
| 3,270,036 | 8/1966 | Bernstein et al. | 260/343.7 |
| 3,489,802 | 1/1970 | Brake | 260/563 |
| 3,501,511 | 3/1979 | Narayanan | 260/397.7 |
| 4,100,170 | 7/1978 | Shetty | 424/325 |
| 4,351,847 | 9/1982 | Griffith et al. | 424/325 |

*Primary Examiner*—Jerome D. Goldberg

[57] ABSTRACT

Treatment of warm-blooded animals infected with the herpes II virus by concurrently orally administering an antiviral agent effective against said virus and suitable for oral administration while topically applying the same or a different such agent to lesions caused by the infection. Effective antivirals include α,α-dimethyl-beta-adamantylethylamine and N,N-dialkyl,α,α-dimethyl-beta-adamantylethylamine.

4 Claims, No Drawings

HERPES II TREATMENT

This application is a continuation-in-part of Serial No. 277,777, filed 6-26-81 now U.S. Pat. No. 4,351,847, dated Sept. 28, 1982.

BACKGROUND OF THE INVENTION

The Invention relates to a method of treating herpes virus, type II in warm-blooded animals with an antiviral composition wherein the agent is applied topically to the infected site while concurrently being administered by absorption into the blood stream through the digestive tract. The invention also comprehends a kit of medication suitable for treating herpes II wherein compositions of such agent, suitable for both oral administration and topical application are provided whereby the patient may begin oral administration prior to, or no later than after, appearance of lesions and use both treatments to alleviate the symptoms. Particularly suitable as an effective antiviral agent for either or both the oral or topical application forms are $\alpha,\alpha$-dimethyl-beta-adamantylethylamines and compositions containing such an agent and at least one pharmaceutically acceptable carrier.

Herpes II is a form of herpes virus that causes a highly infectious venereal disease which is marked by painful lesions in the genital area. In its other forms, herpes causes maladies ranging from common cold sores, chicken pox, and shingles to infectious monoucleosis, and rarer diseases including hepatitis and encephalitis. Reactions to the herpes II infections can range from minor discomfort to incapacitating pain. The disease poses health threats to women and the newborn. There is a high correlation between genital herpes infections and cervical cancer. The newborn child is endangered if birth takes place during an eruptive episode of the disease; there is particular danger to the ocular, labial and genital areas; and skin infections are also common. Blindness and death in the newborn child are not infrequent. Physicians usually resort to delivery of the baby by cesarean section.

U.S. Pat. Nos. 3,270,036, 3,489,802 and 3,501,511 teach various adamantylamine and adamantylalkylamine derivatives as being useful as hypoglycemic agents and antiviral agents for specific viruses, usually influenza, vaccinia, and arbovirus. In clinical practice, those adamantyl alkyl amines have shown utility only against influenza viruses and only if treatment is prophylactic; treatment after the infection is ineffective.

U.S. Pat. No. 4,100,170 teaches adamantylethylamines that are useful as anorexic agents and the parent patent of this application, U.S. Pat. No. 4,351,847 teaches use of either oral or topical application of pharmaceutically suitable compositions of $\alpha,\alpha$-dimethyl-beta-adamantylethylamines for preventing or treating herpes, type II in warm-blooded animals.

SUMMARY OF THE INVENTION

In accordance with the present invention, a warm-blooded animal infected with or about to be exposed to the herpes II virus is treated by orally administering an anti-viral agent, in suitable pharmaceutical form and effective to control said virus, prior to or after exposure of the animal to the virus followed by topical application of the same or different such agent in suitable pharmaceutical form to the site of lesions caused by the virus, the two types of treatment continuing concurrently until healing of the lesions; thereafter oral administration may be continued until danger of further lesion eruption disappears. The invention also comprehends a kit of medications suitable for prophylaxis against and treatment for herpes II virus wherein one or more antiviral agents are packaged together to provide a pharmaceutically suitable oral and topical forms of the antiviral agents. The $\alpha,\alpha$-dimethyl-beta-adamantylethylamines, the N,N-lower alkyl analogues and the acid addition salts of such compounds are particularly useful as an anti-viral agent for this purpose. Usually the antiviral agent is used for medicinal purposes in a conventional extending agent or excipient in the form of a solution, tablet or capsule for oral administration or as a component of an ointment or cream for topical application although the specific identity of the extending agent or excipient is not critical.

DETAILED DESCRIPTION OF THE INVENTION

The crux of the present invention is the manner in which the anti-viral agent effective for treating the herpes II virus is applied to the animal in need of treatment. The effectiveness of the $\alpha,\alpha$-dimethyl-beta-adamantylethylamines in various dosage forms and in various pharmaceutical carriers suitable for both oral and topical administration is disclosed in U.S. Pat. No. 4,351,847 referred to above and which is incorporated herein by reference. The present invention demonstrates that particular effectiveness in the treatment of herpes II is observed when there is a concurrent topical and oral administration of the effective anti-viral agent.

In the Examples cited below, oral treatment is provided by a solution of the $\alpha,\alpha$-dimethyl-beta-adamantylethylamines dissolved in water at the dosages indicated while topical application is made using a solution of the same anti-viral agent in polyvinyl alcohol. The Examples are cited to illustrate the invention they are not intended to limit it in any manner.

EXAMPLE 1

Various groups of female mice were inoculated with herpes II to induce intra-vaginal lesions. Treatment was initiated 24 hours after innoculation. All of the animals were observed and scored in a system for evaluating the severity of the lesion. A scale of 0 to 4 was used to score the animals where 0 meant that no lesion was formed (i.e., normal); 1 meant that a 1–2 mm perivaginal redness and swelling had developed; 2 meant that a 2–3 mm perivaginal redness and swelling had developed; 3 meant that a 3–4 mm perivaginal and perianal redness and swelling had developed; and 4 meant that a greater than 4 mm perivaginal and perianal redness and swelling with discharge had developed.

Calculations for antiviral activity of the drug were based on the average of the daily average scores for the fourth, fifth and sixth days for each group of animals. The difference between the control group and the test group is termed the inhibition score which is a measure of the drug's antiviral activity and is expressed as percentage.

Large numbers of the animals were observed to develop encephalitis causing death. The number of survivors among the total tested was reported and also the mean survival time in days. The results are reported in Table I.

TABLE I

| Treatment Group | Topical Dosage[1] | Oral Dosage[2] | Survivors/ Total | Mean Survival Time[3] (days) | Total Virus Lesion Score | Score Inhibition (%) |
| --- | --- | --- | --- | --- | --- | --- |
| (A) | 1% | H$_2$O | 9/10 | 10.0 | 5.2 | 22 |
| (A) | 5% | H$_2$O | 7/10 | 9.5 | 3.0 | 55 |
| (B) | PVA | 50 mg/kg/day | 1/9 | 16.8 | 5.5 | 18 |
| (B) | PVA | 75 mg/kg/day | 3/9 | 12.3 | 6.1 | 8 |
| (C) | 1% | 75 mg/kg/day | 5/5 | 25.0+ | 3.7 | 44 |
| (C) | 5% | 75 mg/kg/day | 9/9 | 25.0+ | 3.2 | 52 |
| (D) | PVA | H$_2$O | 5/19 | 10.5 | 6.7 | |

[1]PVA indicates no anti-viral agent
[2]H$_2$O indicates no anti-viral agent
[3]Mean survival time of animals dying on or before day 21.

Referring to Table I it will be noted that in Group (C), the only group among those in the table which received both oral and topical treatment, there were no deaths of animals treated and a high score of inhibition of lesions was observed.

EXAMPLE 2

This example illustrates the activity of an antiviral agent in a properly adjusted dosage depending upon the size, weight and nature of the warm-blooded animal. In this example, all treatment was by oral administration from an aqueous solution; the animals were innoculated before medication. The results are reported below in Table II.

TABLE II

| | | Mean Viral Lesions Score Inhibition | |
| --- | --- | --- | --- |
| Treatment Group | Dosage mg/kg/day | Infected, Treated 6 hrs. later | Infected, Treated 24 hrs. later |
| (E) | 100 | 46% | 50% |
| (F) | 75 | 33% | 13% |
| (G) | 50 | 0 | 0 |

From the above it will be noted that the more concentrated dosages were more effective for treatment.

Many equivalent modifications of the above invention will be apparent to those skilled in the art from a reading of the above without a departure from the inventive concept.

What is claimed is:

1. A process for the treatment of herpes II virus in a warm blooded animal comprising administering to said animal in need of said treatment an amount effective for said treatment of an anti-viral agent of the formula given below or the acid addition salt thereof;

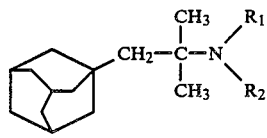

wherein R$_1$ and R$_2$ are selected from the class consisting of H and lower alkyl, said agent being administered orally in conjunction with a topical application in the area of lesions resulting from herpes II virus of said anti-viral agent.

2. The process of claim 1 wherein R$_1$ and R$_2$ are hydrogen.

3. The process of claim 1 wherein both the oral and topical administrations of said compound is in association with at least one pharmaceutically acceptable carrier, said compound constituting from about 0.01 to 95% by weight of the composition resulting from said compound and said carrier.

4. The process of claim 3 wherein said oral administration is with a sustained release form of said compound.

* * * * *